United States Patent
Tate et al.

(10) Patent No.: US 8,552,223 B2
(45) Date of Patent: Oct. 8, 2013

(54) METHOD FOR MAKING HETEROGENOUS CATALYSTS

(75) Inventors: James Tate, New Castle, DE (US); Jose Antonio Trejo-O'Reilly, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 22 days.

(21) Appl. No.: 13/168,119

(22) Filed: Jun. 24, 2011

(65) Prior Publication Data

US 2012/0004468 A1   Jan. 5, 2012

Related U.S. Application Data

(60) Provisional application No. 61/360,287, filed on Jun. 30, 2010.

(51) Int. Cl.
*C07C 45/73* (2006.01)
*B01J 31/08* (2006.01)
*B01J 37/04* (2006.01)

(52) U.S. Cl.
USPC ............ 568/396; 502/159; 502/224; 502/229

(58) Field of Classification Search
USPC .......................... 568/396; 502/159, 224, 229
See application file for complete search history.

(56) References Cited

U.S. PATENT DOCUMENTS

| | | | |
|---|---|---|---|
| 3,493,343 A | 2/1970 | Logan et al. | |
| 3,668,271 A | 6/1972 | Haag | |
| 6,977,314 B2 | 12/2005 | Vandersall et al. | |
| 2003/0215383 A1 | 11/2003 | Escrig et al. | |
| 2008/0051282 A1 | 2/2008 | Fanson et al. | |
| 2009/0127201 A1 | 5/2009 | Kobayashi | |

FOREIGN PATENT DOCUMENTS

| | | |
|---|---|---|
| DE | 1952481 A1 | 4/1971 |
| EP | 1321450 A2 | 6/2003 |
| WO | WO2010106925 A1 | 9/2010 |

OTHER PUBLICATIONS

Ionel Halaciuga, et al; Precipitation of dispersed silver particles using acetone as reducing agent ; Journal of Colloid and Interface Science 354, (2011) 620-623.

Benedetto Corain and Milan Kralik; Dispersing metal nanoclusters inside functional synthetic resins: scope and catalytic prospects; Journal of Molecular Catalysis A: Chemical 159 (2000) 153-162.

A.M. Caporusso, P. Innocenti, L. A. Aronica, G. Vitulli, R. Gallina, A. Biffis, M. Zecca, B. Corain; Functional resins in palladium catalysis: promising materials for Heck reaction in aprotic polar solvents; Journal of Catalysis 234 (2005) 1-13.

B. Corain, P. Centomo, S. Lora, M. Kralik; Functional resins as innovative supports for catalytically active metal nanoclusters; Journal of Molecular Catalysis A: Chemical 204-205 (2003) 755-762.

Benedetto Corain, Milan Kralik; Generating palladium nanoclusters inside functional cross-linked polymer frameworks; Journal of Molecular Catalysis A: Chemical 173 (2001) 99-115.

Benedett Corain, Claudio Burato, Paolo Centomo, Silvano Lora, Wolfgang Meyer-Zaika, Gunter Schmid; Generation of size-controlled gold (0) and palladium (0) nanoclusters inside the nanoporous domains of gel-type functional resins Part I: Synthetic aspects and first catalytic data in the liquid phase; Journal of Molecular Catalysis A:Chemical 225 (2005) 189-195.

Gasparovicova, et al, "PD-CU Supported on Anionic Polymers", Collected Czechoslovakian Chemical Communications, vol. 64, pp. 502-514, 1999.

*Primary Examiner* — Sikarl Witherspoon
(74) *Attorney, Agent, or Firm* — Tifani M. Edwards

(57) ABSTRACT

A method of making a heterogeneous catalyst, the catalyst produced therefrom, and the use of the catalyst, comprising mixing a dried ion exchange resin with a solution of a ketone and a metal, swelling the ion exchange resin, distributing the metal in the resin, and transforming without reducing agents the metal to zero valent at a temperature below 120° C.

8 Claims, No Drawings

METHOD FOR MAKING HETEROGENOUS CATALYSTS

This application claims the benefit of priority under 35 U.S.C. §119(e) of U.S. Provisional Patent Application No. 61/360,287 filed on Jun. 30, 2010.

This invention relates to methods for making heterogeneous catalysts. More particularly, this invention relates to methods for making metal-doped ion exchange resin catalysts.

Methods for making heterogeneous catalysts are known. One method of making heterogeneous catalysts is disclosed in U.S. Pat. No. 6,977,314, where cation exchange resins are loaded with metal ion by contacting an aqueous solution containing such metal with the ion exchange resin followed by a rinse. The catalyst is activated prior to its use in the application. The activation procedure is done by reducing the metal impregnated cationic exchange resin with reducing agents such as hydrogen and hydrazine, which is highly toxic.

In known methods, the resin that is used is in a wet state, where it requires long contact times for the metal to diffuse from liquid into the ion exchange resin beads.

The invention seeks to improve upon the current art by providing a method of making a heterogeneous catalyst with a zero valence state metal homogeneously dispersed in a resin, where the reaction produces less excess liquid and does not require the activation step with the reducing agents known in the art, including hydrogen or hydrazine.

In a first aspect of the invention, there is provided a method of making a heterogeneous catalyst comprising mixing a dried ion exchange resin with a solution of a ketone and a metal, swelling the ion exchange resin, distributing the metal in the resin, and transforming without reducing agents the metal to zero valent at a temperature below 120° C.

In a second aspect of the invention, there is provided a method of making a heterogeneous catalyst comprising mixing a dried ion exchange resin with a solution of a ketone and a metal of palladium, platinum, iridium, rhodium, ruthenium, copper, gold, and/or silver, swelling the ion exchange resin, distributing the metal in the resin such that the metal comprises 0.1 to 15% by weight on a dry basis of the catalyst, and transforming without reducing agents the metal to zero valent at a temperature below 120° C.

In a third aspect of the invention, there is provided a heterogeneous catalyst made by the method of the invention.

In a fourth aspect of the invention, there is provided a use of the heterogeneous catalyst made by the method of the invention for a reaction selected from aldol condensation, dehydration, dimerization, reduction, oxidation, alkylation, etherification, esterification, alkylation, and hydrogenation of alkynes, alkenes, aldehydes, ketones, alcohols, nitriles, amines, and/or nitro groups.

The invention is directed to a method of making a heterogeneous catalyst. A heterogeneous catalyst is a material that is present as a solid phase in a reaction that can have other phases, such as liquid, vapor or gas, that react on the catalyst active site surface rendering products. The heterogeneous catalyst is not soluble in the gas, liquid or vapor phase during the process.

In the method, the catalyst is prepared by mixing a dried ion exchange resin that is dry or partially dry (at least 50% of liquid is removed) with a solution of a ketone and a metal. In one embodiment, a wet ion exchange resin is dried. Examples of ion exchange resins include undersulfonated resins and polysulfonated resins. In a preferred embodiment, the dried ion exchange resin comprises a polysulfonated cation exchange resin, where the range of aromatic/sulfonic is from 10:1 to 1:2. The 1:2 is the sulfonation limit. Other resins that may be used for catalysis include acrylic backbone resins, such as weak acid cation resins, weak base anion resins, strong base anion resins and strong acid cation resins.

The ion exchange resins useful in the method may be in the form of a gel or macroporous beads. Preferably, the ion exchange resin catalysts are in the form of macroporous spherical beads having average particle diameters from 100 µm to 2 mm, more preferably, from 150 µm to 1.5 mm, and most preferably, from 250 to µm to 1 mm. When the ion exchange resin is a polysulfonated cation exchange resin, the content of the sulfonic acid group comprises, preferably, about 5.0 to 7.0, more preferably, about 5.1 to 6.5, and most preferably, about 5.2 to 6.0 meq/g (milliequivalents/gram), based on the dry weight of the polysulfonated cation exchange resin and is loaded with, preferably, about 0.1 to 10%, more preferably, about 0.5 to 5%, and most preferably, about 0.7 to 2%, of metal or metal ion, based on the dry weight of polysulfonated cation exchange resin.

Preferably, the ion exchange resin possesses a surface area from about 10 to 1000, more preferably, about 15 to 500, and most preferably, about 0.1 to 50 square meters/gram ($m^2/g$) and, preferably, has a total porosity of about 0.1 to 0.9, more preferably, about 0.2 to 0.7, and most preferably, about 0.25 to 0.5 cubic centimeter pores per gram of polymer ($cm^3/g$), with an average pore diameter of, preferably, about 50 to 2,500 Angstroms and more preferably, about 150 to 1000 Angstroms.

The ion exchange resins may be prepared from crosslinked macroporous copolymers, which are polymers or copolymers polymerized from a monomer or mixture of monomers containing at least 1 weight percent, based on the total monomer weight, of polyvinyl unsaturated monomer. The porosity is introduced into the copolymer beads by suspension-polymerization in the presence of a porogen (also known as a "phase extender" or "precipitant"), that is, a solvent for the monomer, but a non-solvent for the polymer.

A crosslinked macroporous copolymer preparation, for example, may include preparation of a continuous aqueous phase solution containing suspension aids (such as dispersants, protective colloids and buffers) followed by mixing with a monomer mixture containing 1 to 85% polyvinylaromatic monomer, free-radical initiator, and, preferably, about 0.2 to 5, more preferably, about 0.3 to 3, and most preferably, about 0.4 to 1, parts porogen (such as toluene, xylenes, ($C_4$-$C_{10}$)-alkanols, ($C_6$-$C_{12}$)-saturated hydrocarbons or polyalkylene glycols) per one part monomer. The mixture of monomers and porogen is then polymerized at an elevated temperature and the porogen is subsequently removed from the resulting polymer beads by various means, for example, toluene, xylene and ($C_4$-$C_{10}$)alcohols may be removed by distillation or solvent washing and polyalkylene glycols may be removed by water washing. The resulting macroporous copolymer is then isolated by conventional means, such as dewatering followed by drying.

Suitable polyvinylaromatic monomers that may be used in the preparation of the crosslinked copolymers include, for example, one or more monomers selected from divinylbenzene, trivinylbenzene, divinyltoluene, divinylnaphthalene and divinylxylene, and mixtures thereof; it is understood that any of the various positional isomers of each of the aforementioned crosslinkers is suitable. In a preferred embodiment, the polyvinylaromatic monomer is divinylbenzene. Preferably, the crosslinked copolymer comprises about 1 to 85%, more preferably, about 5 to 55%, and most preferably, about 10 to 25%, polyvinylaromatic monomer units.

Optionally, non-aromatic crosslinking monomers, such as ethyleneglycol diacrylate, ethyleneglycol dimethacrylate, trimethylolpropane triacrylate, trimethylolpropane trimethacrylate, diethyleneglycol divinyl ether, and trivinylcyclohexane, may be used in addition to the polyvinylaromatic crosslinker. When used, the non-aromatic crosslinking monomers preferably comprise as polymerized units, from about 0 to 10%, more preferably, about 0 to 5%, and most preferably, about 0 to 2% of the macroporous polymer, based on the total monomer weight used to form the macroporous copolymer.

Suitable monounsaturated vinylaromatic monomers that may be used in the preparation of crosslinked copolymers include, for example, styrene, α-methylstyrene, $(C_1$-$C_4)$ alkyl-substituted styrenes, halo-substituted styrenes (such as dibromostyrene and tribromostyrene), vinylnaphthalene, and vinylanthracene. Preferably, the monounsaturated vinylaromatic monomer is selected from styrene, $(C_1$-$C_4)$alkyl-substituted styrenes, and mixtures thereof. Included among the suitable $(C_1$-$C_4)$alkyl-substituted styrenes are, for example, ethylvinylbenzenes, vinyltoluenes, diethylstyrenes, ethylmethylstyrenes, and dimethylstyrenes. It is understood that any of the various positional isomers of each of the aforementioned vinylaromatic monomers is suitable. Preferably, the copolymer comprises about 15 to 99%, and more preferably, about 75 to 90%, monounsaturated vinylaromatic monomer units.

Optionally, non-aromatic monounsaturated vinyl monomers, such as aliphatic unsaturated monomers, for example, vinyl chloride, acrylonitrile, (meth)acrylic acids, and alkyl (meth)acrylates, may be used in addition to the vinylaromatic monomer. When used, the non-aromatic monounsaturated vinyl monomers may comprise as polymerized units, preferably, from about 0 to 10%, more preferably, from about 0 to 5%, and most preferably, from about 0 to 2% of the macroporous copolymer, based on the total monomer weight used to form the macroporous copolymer.

Porogens useful for preparing macroporous copolymers include hydrophobic porogens, such as $(C_7$-$C_{10})$aromatic hydrocarbons and $(C_6$-$C_{12})$saturated hydrocarbons, and hydrophilic porogens, such as $(C_4$-$C_{10})$alkanols and polyalkylene glycols. Suitable $(C_7$-$C_{10})$aromatic hydrocarbons include, for example, one or more of toluene, ethylbenzene, ortho-xylene, meta-xylene and para-xylene; it is understood that any of the various positional isomers of each of the aforementioned hydrocarbons is suitable. Preferably, the aromatic hydrocarbon is toluene or xylene or a mixture of xylenes or a mixture of toluene and xylene. Suitable $(C_6$-$C_{12})$ saturated hydrocarbons include, for example, one or more of hexane, heptane and isooctane; preferably, the saturated hydrocarbon is isooctane. Suitable $(C_4$-$C_{10})$alkanols include, for example, one or more of isobutyl alcohol, tert-amyl alcohol, n-amyl alcohol, isoamyl alcohol, methyl isobutyl carbinol (4-methyl-2-pentanol), hexanols and octanols; preferably, the alkanol is selected from one or more $(C_5$-$C_8)$ alkanols, such as, methyl isobutyl carbinol and octanol.

Polymerization initiators useful in preparing copolymers include monomer-soluble initiators, such as peroxides, hydroperoxides and related initiators, for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl)peroxydicarbonate, and methyl ethyl ketone peroxide. Also useful are azo initiators, such as azodiisobutyronitrile, azodiisobutyramide, 2,2'-azo-bis(2,4-dimethylvaleronitrile), azo-bis(.α-methylbutyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tort-butyl perbenzoate; more preferably, the initiator is benzoyl peroxide. Use levels of peroxide initiator are, preferably, about 0.3% to 5%, more preferably, about 0.5 to 3%, and most preferably, about 0.7 to 2%, based on the total weight of vinyl monomers.

Preferably, the crosslinked copolymers are selected from divinylbenzene copolymer, styrene-divinylbenzene copolymer, divinylbenzene-ethylvinylbenzene copolymer and styrene-ethylvinylbenzene-divinylbenzene copolymer for use as substrates for the catalysts. These crosslinked copolymers may be functionalized with strong-acid functional groups according to conventional processes for polysulfonation known to those having ordinary skill in the art, as for example, sulfonation with sulfur trioxide ($SO_3$), fuming sulfuric acid or oleum (concentrated sulfuric acid containing sulfur trioxide), and chlorosulfonic acid. Alternatively, monosulfonated cation exchange resin polymers may also be subjected to conventional polysulfonation conditions to provide the polysulfonated cation exchange resin catalysts.

The dried ion exchanger resin is mixed with a solution of a ketone and a metal. Exemplary ketones include acetone, butanone, pentanone, cyclohexanone, hexanone, and mixtures thereof. Exemplary metals include palladium (Pd), platinum (Pt), iridium (Ir), rhodium (Rh), ruthenium (Ru), copper (Cu), gold (Au), silver (Ag), and mixtures thereof. The catalyst is made with a zero valence state metal homogeneously dispersed in the resin.

The ion exchange resin is swelled and the metal is distributed in the resin. The ion exchange resins may be loaded with the desired metal ion by contacting an aqueous solution of the metal ion with the hydrogen form of the ion exchange resin in a batch or continuous reactor. The metal ion may be provided in the form a metal salt, such as, for example, chlorides, bromides, nitrates, sulphates, acetylacetonates, and acetates. The loaded ion exchange resin may be rinsed free of residual salts or acid. The ketone may also be removed from the ion exchange resin during process of making the catalyst. The amount of metal salt used is chosen such that the metal or metal ion will ultimately be present in an amount of about 0.1 to 2% loading, preferably, about 0.5 to 1.5% loading, and more preferably, about 0.8 to 1.2% loading of ion exchange resin. In a preferred embodiment, the ion exchange resin catalysts contain 0.1 to 15% metal based on the dry weight of the catalyst.

In a preferred embodiment, the metal is transformed without reducing agents to zero valent at a temperature below 120° C. The catalyst that is made comprises a yield of about 5-60% with a selectivity of about 70-99%. In one embodiment, the catalyst comprises a yield of 20-35% with a selectivity of 94-99%. Yield is based on the amount of ketone produced, and selectivity is based on the amount of ketone produced relative to the total product. In the method of the invention, excess liquid and liquid waste after the method is minimal or even absent and reduction of the metal is achieved without reducing agents at low temperatures below 120° C. As a result, the dried catalyst produced by the method may be used directly in reducing conditions without pretreatment. Possible reactions with the catalyst, include, but are not limited to, reactions selected from aldol condensation, dehydration, dimerization, reduction, oxidation, alkylation, etherification, esterification, alkylation, and hydrogenation of at least one of alkynes, alkenes, aldehydes, ketones, alcohols, nitriles, amines, and nitro groups.

In one example of the method, 1 liter of ion exchange resin in hydrogen (H) form is poured into a solution of 10-50 grams of palladium acetate in 0.5-2 liters of distilled water, the palladium is allowed to absorb onto the ion exchange resin for about 1 to 4 hours, and then the solution is decanted from the resin. Alternatively, the ion exchange resin may be loaded with metal by passing an aqueous solution of the metal salt through a column of the ion exchange resin until a desired level of metal ion has been retained by the resin. This may be followed by thorough washing with water to remove residual salts and acid generated during the loading process.

In one embodiment of using the catalyst, the metal-doped ion exchange resin catalyst is in the physical form of beads contained in a vessel, the beads forming a bed of the catalyst. A feed stream of ketone reactant, or solvent, such as acetone, is brought into contact with the catalyst bed in the presence of hydrogen (as a separate feed stream) for a sufficient time and temperature for a condensation reaction of the ketone to occur. The condensed liquid stream, containing reaction products (saturated ketone adduct), byproducts (unsaturated ketone adduct), and any unreacted ketone reactant that may be present, is separated from the catalyst bed, and desired ketone adduct is recovered from the liquid stream by conventional separation means (such as distillation).

One of ordinary skill in the art will be able to choose appropriate conditions, such as (1) batch operation, for example, in which the catalyst bed is loaded with the liquid stream in the presence of hydrogen, or (2) the more preferred continuous operation, for example, where the liquid stream is fed continuously into one end of a column reactor (with hydrogen) at a rate that allows sufficient residence time in the catalyst bed for the desired reaction to occur, with the condensed liquid stream being removed continuously from the other end of the bed Similarly, the reaction equipment, the choice of upflow or downflow for the direction of passage of the reactant streams through the bed, the reaction time and temperature, the particular reactants, and the method of recovering the ketone adduct, are readily selected based upon the guidance provided herein and the knowledge available to one of ordinary skill in the art.

The temperatures and pressures inside the column reactor may be selected so that the ketone reactant is at its boiling point in the catalyst bed. Variation of temperature/pressure of the ketone reactant is used to provide the desired combination of reaction temperature and conditions such that the condensation reaction takes place in the liquid phase in the catalyst bed. Conditions may be varied to provide gas phase conditions with the catalyst bed, and the conditions may be such that the condensation reaction is conducted in the liquid phase. In a preferred embodiment, a trickle bed condition, where there is liquid and gas flowing through the catalyst bed, is used. In one embodiment, the gas is hydrogen and the equilibrium liquid/vapor is acetone. Choosing a higher pressure may provide more liquid.

The metal-doped ion exchange resin catalysts of the invention may be used in condensation reactions where the ketone reactant and hydrogen are contacted under batch reaction conditions or under continuous reaction conditions. In one embodiment, the method is a continuous process based on a catalytic distillation process with the introduction of the ketone reactant being into the bottom of a column reactor immediately above a reboiler stage; in this case, the product fraction or stream is withdrawn continuously from the reboiler portion of the distillation apparatus for further processing. Preferably, the ketone reactant to undergo the condensation reaction is fed downward through the catalyst bed and a current of hydrogen is passed through the reaction zone in the same direction. However, other variations of introducing the reactant feed streams may be used, such as co-current and countercurrent hydrogen flow, flooding processes, and gaseous-phase processes.

For continuous processes, the amount of catalyst to be used, relative to the amount of reactants, is typically related to the throughput rate of the reactions, as indicated by the LHSV (liquid hourly space velocity) or liquid flow rate of reactants relative to the volume of catalyst per unit time. High LHSV may be desirable to maximize equipment usage and generation of product; however, meeting this objective must be balanced against % conversion of raw materials and % selectivity to the desired product. If the LHSV is too low, production rate of the desired product (yield and selectivity) is diminished, and the process may not be economical. If the LHSV is too high, the catalyst activity will be insufficient to provide the desired level of conversion (the process becomes "kinetically limited"). Suitable values of LHSV will typically range from, preferably, 0.5 and 10 $h^{-1}$, more preferably, from 1 to 8 $h^{-1}$, and most preferably, from 2 to 4 $h^{-1}$.

The ketone reactant may be contacted with hydrogen in the presence of the catalyst at a temperature of 65 to 200° C. and at a pressure from 1 to 100 bar (0.1 to 10 MPa) of hydrogen. Typically, the condensation reaction is conducted at a hydrogen/ketone reactant molar ratio of at least 1:1.

In another embodiment, the process may be a batch reaction with the introduction of the ketone reactant into a reactor column at the reboiler section stage of a catalytic distillation apparatus (similar to that described above). The process may then be terminated when a desired product composition of ketone adduct is achieved in the reboiler section. Alternatively, the condensation may be carried out in a batch autoclave reactor for a specified period of time, followed by cooling and recovery of the desired amount of the ketone adduct by distillation or other conventional means.

The following examples are presented to illustrate the invention. In the examples, the following abbreviations have been used.

GC is gas chromatograph.
keV is kiloelectron Volt.
kPa is kilopascal.
kV is kilovolt.
LHSV is liquid hourly space velocity.
mA is milliAngstrom; μA is microAngrstrom.
MIBK is methyl isobutyl ketone.
MPa is megaPascal.
psi is pounds per square inch.
RPM is rotations per minute.
W is Watt.
C is Celsius; ml is milliliter; μl is microliter; min is minute; h is hour; sec and s is second; g is gram; m is meter; cm is centimeter; nm is nanometer; mm is millimeter; μm is micrometer or micron; cc is cubic centimeter; and nml/min is milliliter per minute at gas standard conditions defined as pressure=1 atm, temperature=25° C., and volume=22.4 liters.

Test Methods

Scanning Electron Microscopy (SEM): To provide a conductive coating for SEM imaging, samples were either sputter-coated with a gold/palladium alloy or, alternatively, a carbon coating was evaporated onto the samples. The sputter-coated samples were primarily used for imaging and the carbon-coated samples were primarily used for elemental analysis. Images of iron-coated limestone in a dry state were taken with both a JEOL 840 SEM and a JEOL 6700 FESEM ("field emission scanning electron microscope"), both available from JEOL USA, Peabody, Mass., with an accelerating voltage of between 10 and 20 keV. Images from the JEOL 840 were taken using PGT Imix-PC software, available from Princeton Gamma-Tech Instruments, Inc., Princeton, N.J., and images from the JEOL 6700 were taken with JEOL's PC-SEM software. Energy dispersive x-ray spectroscopy ("EDS" or "EDX") spectra and elemental maps were taken with a PGT detector, using PGT Imix-PC software. Magnifications of between 100× and 300× were used for images intended for measurement of the coating thickness. Spatial calibrations and coating thickness measurements were generated with Image-Pro Plus™ image analysis software from Media Cybernetics, Silver Spring, Md. Selected limestone and charcoal particles were cut in half with a scalpel and the resulting cut surfaces were oriented as close as possible to perpendicular to the electron beam in order to examine the penetration of iron by EDS.

Experimental Conditions:

| Light microscopy | |
| --- | --- |
| Microscope | Olympus SZX stereoscope |
| Camera | QImaging Retiga 2000R |
| Magnifications | 7x |
| SEM | |
| Instrument | JEOL 6700 FESEM |
| Accelerating Voltage | 2 keV |
| Emission current setting | 20 µA |
| Probe current setting | 8 |
| Detector | LEI |
| Working distance | 8 mm |
| Coating | Au/Pd 40 sec. w/ Denton Desk II |
| Magnifications | 100x, 2,000x, 20,000x |

X-Ray Fluorescence (XRF): The samples were analyzed using a Philips/PANalytical PW2404 Wavelength Dispersive X-Ray Fluorescence Spectrometer from PANalytical, Almelo, The Netherlands. The samples were dried overnight at 110° C. Approximately 1-1.5 g of each sample was weighed in a XRF sample cup with polypropylene film and analyzed under helium. The results were calculated using a Uniquant software package, which is a standardless quantitation package, from Omega Data Systems by, Neptunus 2 NL-5505 NH Veldhoven, The Netherlands. Results were calculated assuming the elements were present in their oxide form except Ca, which is assumed to be $CaCO_3$. The sample was also assumed to be all inorganic. In XRF, an x-ray beam was focused on the sample, which displaced inner shell electrons; outer shell electrons replaced the inner shell electrons and emitted light during this process (or fluorescence) that is equal to the energy difference between them. The wavelength of light emitted is unique to each element and the intensity of the light emitted is proportional to the concentration of the element. Wavelength Dispersive XRF spectrometers use diffraction crystals to separate the various wavelengths of light emitted.

X-ray Diffraction (XRD): Rigaku D/MAX 2500 at 50 kV/200 mA of nickel filtered copper Kα radiation. The samples were scanned from 5 to 85 degrees of 2θ in steps of 0.03 degrees at 0.25 degrees/minute. Reflection geometry was used and samples were rotated at 20 RPM. The bead-like samples were mounted on a layer of stopcock grease in a standard volume sample holder. The beads were in the top layer of the grease and were carefully leveled so as to present the sample on the focusing circle of the diffractometer.

XPS: XPS data was collected on a Thermo K-alpha X-ray Photoelectron Spectrometer. Monochromatic Al Kalpha X-rays (72 W, 12 kV, 6 mA) was used as an excitation source. The analysis area was 100 µm. Pass energies of 20 eV were used to collect high resolution data while 200 eV pass energies were used to collect survey spectra. A take-off angle of 90 degrees was used. CasaXPS software was used to workup the data. Samples were prepared by sprinkling the resins on double sided copper tape. A minimum of 5 beads were analyzed for each sample.

Yield, Conversion, and Selectivity: The product from reaction is injected in a GC chromatograph. The different reaction products were analyzed and quantified. The acetone conversion is the acetone that reacts to make products, the product yield is the amount of wanted product obtained, and the selectivity is the ratio of target product to all the products determined by GC.

Dual Column GC-FID Method Description:
Carrier Gas: $N_2$ from High Pressure house Nitrogen
Injector: 0.2 µl volume
Inlet: Front, Mode: split, Temperature: 250° C., Pressure: 5.4 psi (37 kPa)
Split ratio: 50.0 to 1, Split flow 73.0 ml/min; Total flow 76.6 ml/min
Gas saver: 20.0 ml/min @ 2.00 min
Columns:
Column 1: Macherei Nagel 726600. Optima Wax. 30 m×250 µm×0.25 µm
Constant Pressure, Inlet: Front, Outlet: Front
Nitrogen flow: Pressure 5.4 psi (37 kPa), Flow 0.7 ml/min, Average velocity 20 cm/s
Column 2: Varian CP9151 VF1701MS Capillary 30.0 m×250 µm×0.25 µm
Constant Pressure, Inlet: Front, Outlet: Back
Nitrogen flow: Pressure 5.4 psi (37 kPa), Flow 0.7 ml/min, Average velocity 20 cm/s
Oven:
Setpoint: 40° C.
Hold time: 5 min
Ramp 1: 5.0° C./min to 115° C.
Ramp 2: 15.0° C./min to 240° C.
Final time: 6.67 min @ 240° C.
Total run time: 35 min
Detectors:
Front FID: Heater: 250° C.
Flows: $H_2$: 30 ml/min, Air: 350 ml/min, Makeup $N_2$: 30 ml/min
Signal 1: Data rate 20 Hz, peak width 0.01 min, Start 0, End 35 min
Back FID: Heater: 250° C.
Flows: $H_2$: 30 ml/min, Air: 350 ml/min, Makeup $N_2$: 30 ml/min
Signal 2: Data rate 20 Hz, peak width 0.01 min, Start 0, End 35 min

TABLE 1

Standards for Testing for Yield, Conversion and Selectivity

| Compound Name | CAS # |
| --- | --- |
| Acetone | |
| Benzene, 1,2,4 trimethyl- | 95-63-6 |
| Diacetone alcohol | 123-42-2 |
| Diisobutyl ketone (DMH1) | 108-83-8 |
| 2-Heptanone, 4,6-dimethyl-(DMH2) | 19549-80-5 |
| Isopropyl alcohol | 67-63-0 |
| 4-Methyl-2-pentanol (MIBC) | 108-11-2 |
| Methyl Isobutyl Ketone (MIBK) | 108-10-1 |
| 3-Penten-2-one, 4-methyl-(MSO) | 141-79-7 |
| Pentane, 2-methyl- | 107-83-5 |

EXAMPLES

Example 1

Preparation of Catalyst

Commercial dried ion exchange resin (i.e. Amberlyst™ 36 DRY resin) and Pd salt solution in solvent that has relatively low boiling point (i.e. acetone) were used.

Incipient wetness method procedure: The amount of metal to load into the resin and the liquid needed to swell the resin was calculated. The solution of metal salt was made. The dried resin was mixed with the metal containing solution. The swelling of the resin was achieved and no excess liquid was observed. The material was then dried at a temperature that would evaporate the solvent (that could be recovered). The observation was that the resin color changed to a dark black. Measurements by XPS confirmed that the metal was reduced to zero valent and a portion remained as Pd(II). The catalyst was dry and ready to use in the application as catalyst for any reduction condition. Measurements by XRD determined the presence of Pd crystals and XPS determined valence of the metal corresponding to Pd(0) and Pd(II).

Example 2

Preparation of Pd Catalyst 1 g of strong acid cationic styrenic resin was dried at 110° C. overnight. A solution of acetone and Pd acetate was made. The clear colored solution was contained. The use of Pd was calculated to be 1% by weight on a dry basis of the resin and the total liquid used was calculated to be 5% less than the total swelling capacity of the resin for the selected solvent. The liquid was mixed with the resin and in 30 minutes at room temperature, it was observed that there was no excess liquid in the sample. The material was then dried at 110° C. for 2 hours and the color of the resin was dark black. This catalyst had nanometric Pd clusters determined by XRD to have an estimated crystal size of 40 nm (by Scherrer's equation) and 1.02% Pd as measured by 1 CP.

Example 3

Heterogeneous Catalyst Application 8 g of dried Pd loaded resin were charged to a column and acetone was used to make the slurry of the catalyst. Hydrogen was provided at 300 cc/min, acetone was provided at 0.25 ml/min, and the temperature was 100° C. The column ran at 2 MPa. The product obtained after 3 hours was collected and analyzed in a GC equipment. Acetone conversion and selectivity were reported. Amberlyst™ CH28 catalyst and laboratory prepared catalyst JFT13088 were prepared following Example 2. Conditions: acetone LHSV=2 $h^{-1}$, temperature=120° C., pressure=2 MPa, and hydrogen flow rate=350 nml/min.

| RESIN | Acetone Conversion (%-mol) | MIBK Yield (%-mol) | MIBK-GC Selectivity (%) |
|---|---|---|---|
| AMBERLYST™ CH28 resin[a] | 29 | 27 | 94.1 |
| EXPERIMENTAL CATIONIC RESIN[b] | 30 | 29 | 94.7 |

[a] = Commercial resin reduced with hydrogen prior to MIBK manufacture.
[b] = Experimental resin reduced by procedure in this application and run in MIBK manufacture process.

What is claimed is:

1. A method of making a heterogeneous catalyst comprising:
    mixing a dried ion exchange resin with a solution of a ketone and a metal;
    swelling the ion exchange resin;
    distributing the metal in the resin; and
    transforming without reducing agents the metal to zero valent at a temperature below 120° C.

2. The method of claim 1 wherein the dried ion exchange resin comprises at least one of a dry ion exchange resin and a partially dry ion exchange resin.

3. The method of claim 1 further comprising:
    removing the ketone from the ion exchange resin.

4. The method of claim 1 further comprising:
    drying a wet ion exchange resin.

5. The method of claim 1 wherein the catalyst comprises 0.1 to 15 percent metal ion, based on dry weight of the catalyst, distributed therein, the metal ion selected from one or more of palladium, platinum, iridium, rhodium, ruthenium, copper, gold, and silver.

6. The method of claim 1 wherein the ketone comprises acetone.

7. A heterogeneous catalyst made by the method of claim 1.

8. A method of making a heterogeneous catalyst comprising:
    mixing a dried ion exchange resin with a solution of a ketone and a metal of at least one of palladium, platinum, iridium, rhodium, ruthenium, copper, gold, and silver;
    swelling the ion exchange resin;
    distributing the metal in the resin such that the metal comprises 0.1 to 15% by weight on a dry basis of the catalyst, and
    transforming without reducing agents the metal to zero valent at a temperature below 120° C.

* * * * *